(12) United States Patent
Kawula et al.

(10) Patent No.: US 7,155,292 B2
(45) Date of Patent: Dec. 26, 2006

(54) ACTIVE FIXATION ASSEMBLY FOR AN IMPLANTABLE DEVICE

(75) Inventors: Paul Kawula, Sunnyvale, CA (US); Christopher P. Knapp, Ham Lake, MN (US); Carolyn Wineland, Chelsea, MI (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 88 days.

(21) Appl. No.: 10/671,009

(22) Filed: Sep. 25, 2003

(65) Prior Publication Data

US 2005/0070988 A1 Mar. 31, 2005

(51) Int. Cl.
*A61N 1/05* (2006.01)
(52) U.S. Cl. ..................... 607/120; 607/127
(58) Field of Classification Search ......... 607/115–131
See application file for complete search history.

(56) References Cited

U.S. PATENT DOCUMENTS

| | | | | |
|---|---|---|---|---|
| 5,002,067 A | * | 3/1991 | Berthelsen et al. | 607/120 |
| 5,003,992 A | * | 4/1991 | Holleman et al. | 607/120 |
| 5,267,564 A | * | 12/1993 | Barcel et al. | 600/310 |
| 5,324,325 A | * | 6/1994 | Moaddeb | 607/120 |
| 5,447,533 A | | 9/1995 | Vachon et al. | |
| 5,531,780 A | | 7/1996 | Vachon | |
| 5,833,715 A | | 11/1998 | Vachon et al. | |
| 5,871,531 A | | 2/1999 | Struble | |
| 6,086,582 A | | 7/2000 | Altman et al. | |
| 6,298,272 B1 | | 10/2001 | Peterfeso et al. | |
| 6,358,247 B1 | * | 3/2002 | Altman et al. | 606/41 |
| 6,416,510 B1 | | 7/2002 | Altman et al. | |
| 6,478,776 B1 | | 11/2002 | Rosenman et al. | |
| 6,547,787 B1 | | 4/2003 | Altman et al. | |
| 6,569,144 B1 | | 5/2003 | Altman | |
| 6,671,562 B1 | | 12/2003 | Osypka et al. | |
| 6,726,662 B1 | | 4/2004 | Altman | |
| 2002/0156383 A1 | | 10/2002 | Altman et al. | |
| 2004/0002692 A1 | | 1/2004 | Claude et al. | |

FOREIGN PATENT DOCUMENTS

EP 0414233 A2 2/1991
WO WO-0126706 4/2001

OTHER PUBLICATIONS

Guidant Corporation, "Physican's Manual EASYTRAK 2", *Guidant Physican's Manual, Models 4515/4517/4518/4520*, (2002) 30 pgs.
"International Search Report for corresponding PCT Application No. PCT/US2004/031538", (Jan. 24, 2005) ,4 pages.

* cited by examiner

*Primary Examiner*—Scott M. Getzow
(74) *Attorney, Agent, or Firm*—Schwegman, Lundberg, Woessner, & Kluth, P.A.

(57) ABSTRACT

An implantable device such as a lead is adapted for implantation on or about the heart and for connection to a system for monitoring or stimulating cardiac activity. The implantable device includes an active fixation assembly for securing the device to tissue. The active fixation assembly includes one or more recessed portions therein.

30 Claims, 6 Drawing Sheets

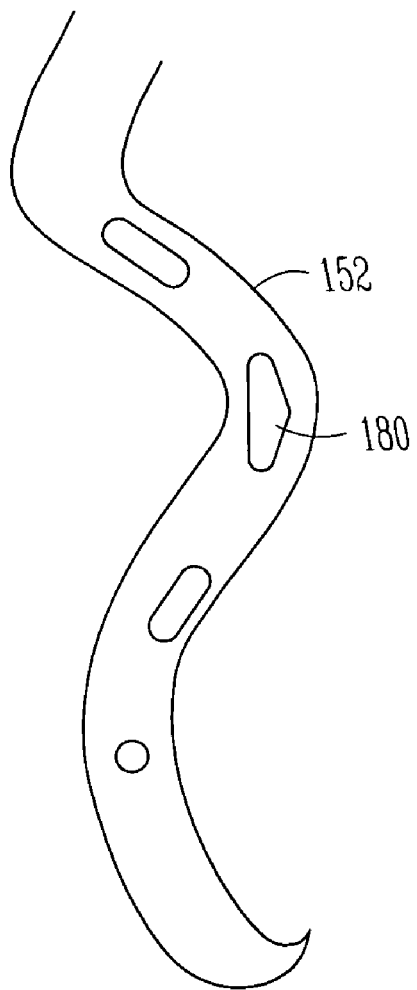
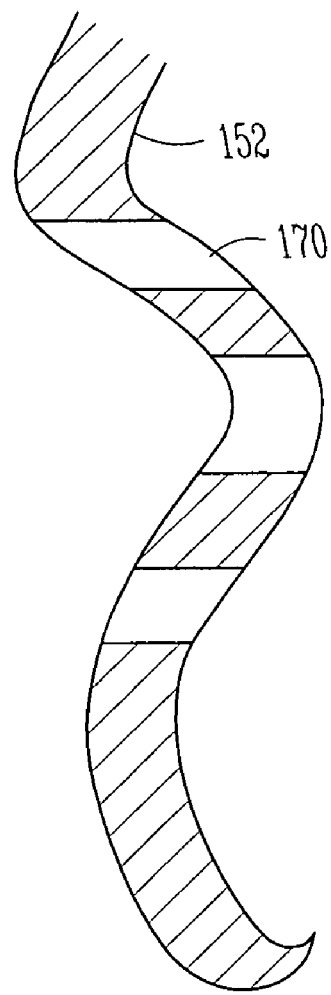
Fig. 4A
Fig. 4B

ACTIVE FIXATION ASSEMBLY FOR AN IMPLANTABLE DEVICE

TECHNICAL FIELD

Leads for conducting electrical signals to and from the heart, and more particularly, a fixation assembly for coupling a lead with tissue.

TECHNICAL BACKGROUND

Pacemaker leads represent the electrical link between the pulse generator and the heart tissue which is to be excited. These pacemaker leads include single or multiconductors that are connected to an electrode in an electrode assembly at a distal end of a pacing lead. Typically, a terminal member is mounted within a flexure sleeve at the proximal end of the pacing lead and connected to the proximal end of the conductor.

After the electrode assembly is positioned at a desired location within the heart, it is desirable to provide some method for securing the electrode assembly at that location. Mechanical fixation devices are used to firmly anchor the electrodes in the heart. One type of mechanical fixation device used is a corkscrew, or a helix. The helix is extended and screwed into the heart muscle by applying a torque to the other end of the conductor or by rotating the lead itself. Once the lead is inserted into the tissue, the tissue undergoes trauma, and will attempt to repair itself.

Some leads include drug eluting structures proximate the electrodes to deliver therapeutic drugs near the electrode/tissue interface. However, current leads utilize a drug plugs collar to store and control the release of the drugs. However, as leads become smaller, the size of the drug plugs and collars becomes incompatible with the lead size.

There is a need for a body-implantable lead that has a helix for fixation to the wall of the atrium or ventricle of the heart. In addition, there is a need for an active fixation helix that minimizes trauma to the tissue.

SUMMARY

An implantable device including a device body. The implantable device further includes an active fixation assembly coupled with a portion of the implantable device, where the active fixation assembly having one or more cavities therein.

Several options for the implantable device exist, some of which are as follows. For example, in one option, the active fixation assembly is a fixation helix, and optionally forms the electrode for the implantable device. In another option, a drug eluting substance is disposed within the one or more cavities. In yet another option, the active fixation assembly includes a hypotube having a lumen therein. The at least one of the one or more cavities, in one option, extends from a first side of the active fixation assembly to a second side of the active fixation assembly, forming a passage therethrough.

In one embodiment, an implantable device includes a device body, and at least one conductor disposed within the device body. The implantable device further includes an active fixation assembly coupled with a portion of the implantable device, where the active fixation assembly has at least one reservoir therein. The active fixation assembly further includes an outer surface and at least one passage that extends from the outer surface to the one or more reservoirs.

In one option, at least one of a drug or a therapeutic agent is disposed within the at least one reservoir. In another option, a plug is disposed within the at least one passage, where the plug optionally includes at least one of a polymer, gel, or glass frit plugs.

In yet another option, the active fixation assembly is retractable within the device body.

A method is also provided and includes disposing a conductor within an implantable device body, electrically coupling a fixation helix with the conductor, and forming at least one recess within a surface of the helix.

In one option, the method further includes disposing a drug eluting substance within the at least one recess within the helix, and optionally disposing a drug eluting substance within the at least one recess includes disposing a drug filled glass frit within the helix.

These and other embodiments, aspects, advantages, and features will be set forth in part in the description which follows, and in part will become apparent to those skilled in the art by reference to the following description and referenced drawings or by practice thereof. The aspects, advantages, and features are realized and attained by means of the instrumentalities, procedures, and combinations particularly pointed out in the appended claims and their equivalents.

BRIEF DESCRIPTION OF THE DRAWINGS

FIG. 4A is a side elevational view of an active fixation assembly constructed in accordance with one embodiment.

FIG. 4B is a cross-sectional view of the active fixation assembly shown in FIG. 4A.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the spirit and scope of the present invention. Therefore, the following detailed description is not to be taken in a limiting sense, and the scope is defined by the appended claims.

Figure 1:
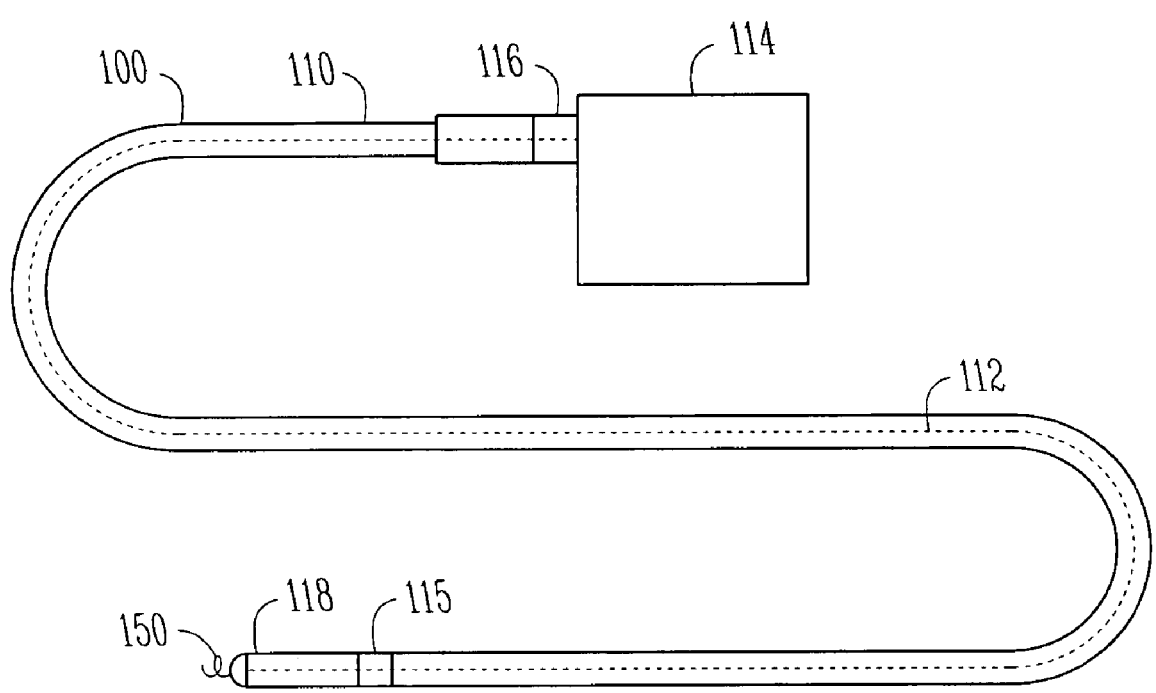
FIG. 1 is a side elevational view illustrating a lead system constructed in accordance with one embodiment.

An implantable device 100, such as a lead for use with an electrical stimulator 114, is illustrated in FIG. 1. The implantable device 100 includes a lead body 110, an elongate conductor 112 contained within the lead body 110. The lead body 110 extends from a proximal end 116 to a distal end 118. The proximal end 116 of the lead is electrically coupled with the electrical stimulator 114, for example, with a connector.

In one option, the electrical stimulator 114 is a pulse sensor and generator that contains electronics to sense various electrical signals of the heart and also produce current pulses for delivery to the heart. The pulse sensor and generator also contain electronics and software necessary to detect certain types of arrhythmias and to correct for them.

The implantable device 100 further includes, in one option, an electrode 115. The electrode 15 is electrically coupled with the at least one conductor 112. The electrode 115 allows for electrical signals to be delivered to the tissue from the electrical stimulator 114. The implantable device 100 further includes an active fixation assembly 150 that allows the device 100 to be coupled with tissue.

Figure 2A:
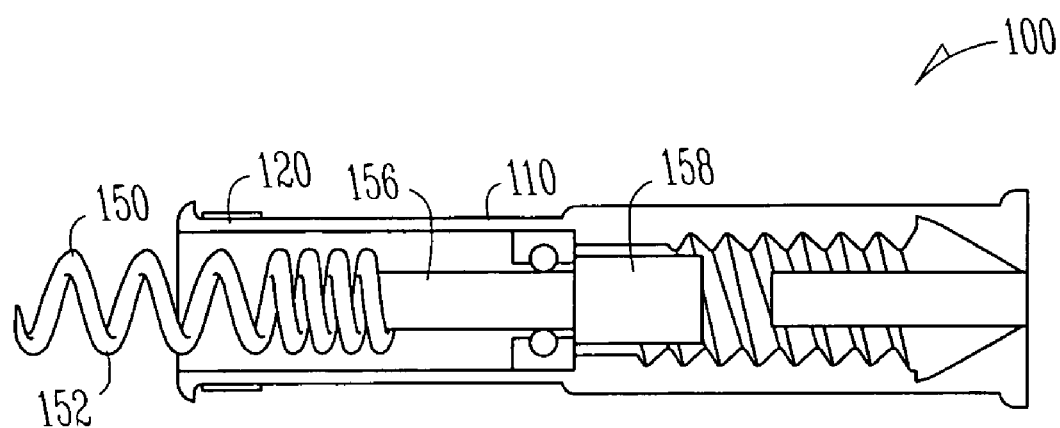
FIG. 2A is a cross-sectional view of a portion of a lead constructed in accordance with one embodiment.
Figure 2B:
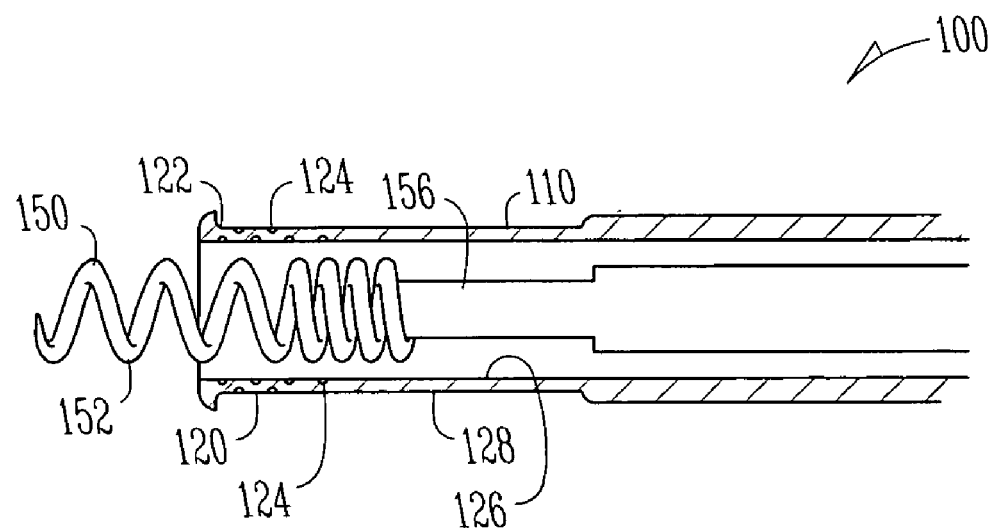
FIG. 2B is a cross-sectional view of a portion of a lead constructed in accordance with another embodiment.

Referring to FIGS. 2A and 2B, the active fixation assembly 150 includes a fixation helix 152. In one embodiment, the helix 152 is formed of electrically conductive material offering low electrical resistance and is also resistant to corrosion by body fluids. A platinum-iridium alloy is an example of a suitable material. Alternatively, the helix 152 is electrically inactive.

In one option, the helix 152 is fixed relative to the lead body 110. To engage the helix 152 with tissue to fixate the helix 152 thereto, the lead body 110 is rotated to rotate the helix 152. In another option, the helix 152 moves relative to the lead body 110, where the helix 152 has a retracted position, for example, during advancement of the device 110 through the vasculature. The helix 152 further includes an extended position, where the helix 152 is extended out of the lead body 110, for example out of the distal end of the lead body 110. For example, the helix 152 is coupled with other components within the device 100 to advance the helix 152.

The helix 152 is coupled with, in one option, an electrode base 156. In one option, the electrode base 156 is used to advance the helix 152 from a retracted position within the distal end 118 of the device 100 to an extended position, as illustrated in FIGS. 2A and 2B. In one option, a distal portion 120 of the device 100 (FIG. 1) forms a housing 122 for the helix 152. In one option, the housing is formed of PEEK material.

The housing 122 in one option, includes one or more recesses 124 therein, as illustrated in FIG. 2B. The one or more recesses 124 form cavities that allow, for example, for drug eluting material to be disposed therein, as further discussed below. In one option, the one or more recesses 124 are formed on an inner surface 126 of the housing 122. In another option, the one or more recesses 124 are formed on an outer surface 128 of the housing 122. It should be noted that the one or more recesses 124 can be formed on the outer surface 128 and/or the inner surface 126 of the housing 122. In yet another option, the one or recesses 124 are formed within the electrode base 156.

In one option, the fixation helix 152 is mechanically, and optionally electrically, coupled with a piston 158. The piston 158, in one option, is configured to mate with a bladed stylet at, for example, a stylet slot, and acts as an interface between the stylet and the helix 152. The stylet, coupled with the piston 158, extends and retracts the fixation helix 152 when the stylet is rotated. The piston 158 can either be electrically active or inactive.

Figure 3C:
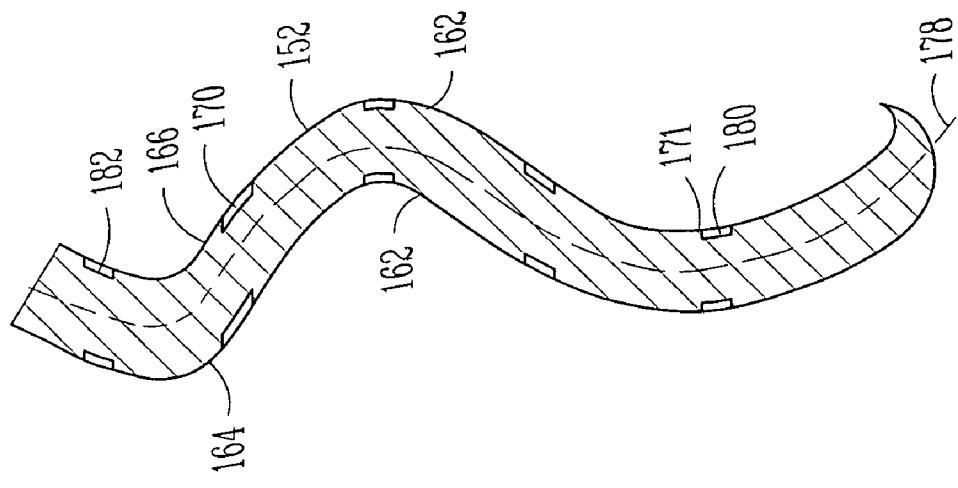
FIG. 3C is a cross-sectional view of the active fixation assembly shown in FIG. 3A in accordance with another embodiment.
Figure 3B:
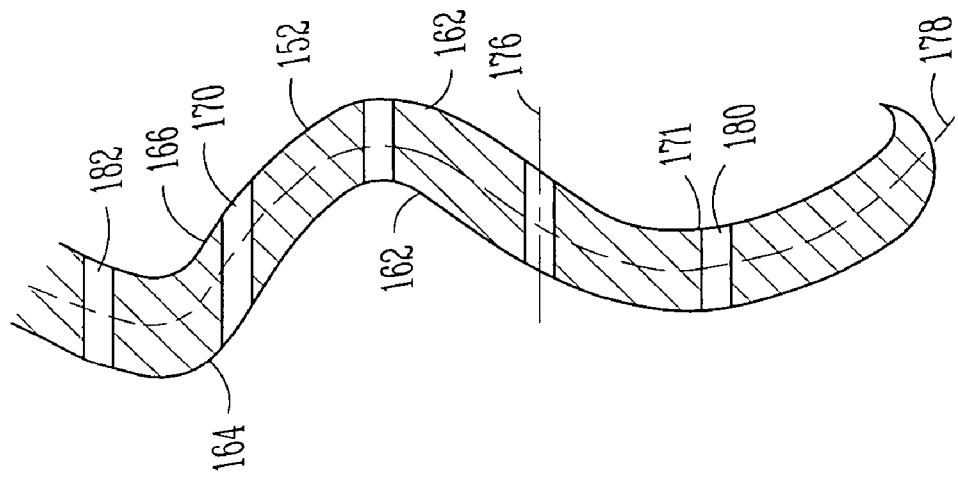
FIG. 3B is a cross-sectional view of the active fixation assembly shown in FIG. 3A in accordance with one embodiment.
Figure 3A:
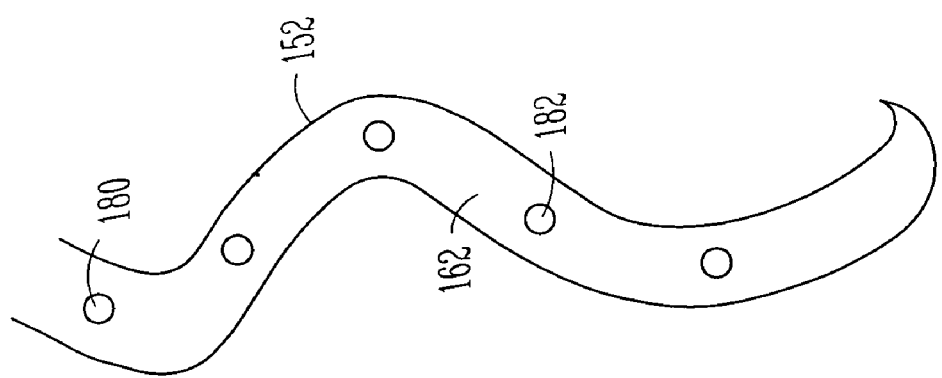
FIG. 3A is a side elevational view of an active fixation assembly constructed in accordance with one embodiment.

FIGS. 3A, 3B, 3C, 4A, 4B, 5A, and 5B illustrate the fixation helix 152 in greater detail. Referring to FIGS. 3A and 3B, the fixation helix 152 includes one or more cavities 180 therein. In one option, the one or more cavities 180 include an aperture 182, such as a circular aperture, formed on an outer surface 162 of the fixation helix 152, which is recessed into a surface of the helix to form a cylindrical shape. In another example, the one or more cavities 180 include a conical shape. In another option, as illustrated in FIGS. 4A and 4B, the one or more cavities 180 include a slotted configuration. While one example of the one or more cavities 180 includes a cylindrical recess, it should be noted that the one or more cavities 180 can have other shapes, depths, cross-sections and configurations. For example, the one or more cavities 180 can be disposed in a random or uniform pattern.

At least a portion of the aperture 182 is recessed into the fixation helix 152 to form the one or more cavities 180. In one option, the one or more cavities 180 are a shallow depression within the fixation helix 152, as illustrated in FIG. 3C. In another option, the one or more cavities 180 are recessed within a portion of the fixation helix 152, to a greater depth than the shallow depression. In yet another option, the one or more cavities 180 extend from a first outer surface 164 to a second outer surface 166 of the fixation helix 152 (FIG. 3B). In another option, the one or more cavities 180 are formed on other portions of the implantable device 100 (FIG. 1), such as on a defibrillation electrode, or on the housing, as discussed above.

Referring again to FIGS. 3A, 3B, 4A, and 4B, the one or more cavities 180 are disposed along a surface of the helix. In one option, the helix is defined in part by a helical axis 178. The helical axis 178 extends helically and longitudinally along the helix 152. In one option, an axis 176 defining in part the one or more cavities 180 is disposed substantially transverse to the helical axis 178. In another option, the axis 176 is disposed at an oblique angle relative to the helical axis 178.

The one or more cavities 180 are, in one option, formed within the fixation helix 152 by laser drilling, micro drilling, electrode discharge machining (EDM), milling, drilling, or a high-energy source to remove material from the fixation helix 152. In one option, the material is mechanically removed from the fixation helix 152 to form the one or more cavities 180. In another option, material is chemically removed from the fixation helix 152 to form the one or more cavities 180. In yet another option, the one or more cavities 180 are formed by molding the fixation helix 152 with the cavities formed as part of the molding process.

In one option, a drug eluting substance 170 is disposed within the one or more cavities 180. The drug eluting substance 170 assists, in one option, with tissue trauma. Examples of such drugs include, but are not limited to, steroids, anti-inflammatory agents, anti-coalgulating agents. In one option, a polymer/drug substance is disposed within the one or more cavities 180. In another option, a glass frit 171 (FIG. 3B) filled with drug, for example, a preloaded glass frit, is disposed within the one or more cavities 180. In another option, a gel-containing drug is disposed within the one or more cavities 180, and in a further option, a gel-containing drug that allows for an assortment of biological agents or release profiles. In one option, the drug eluting substance 170 is sprayed into the one or more cavities 180. In another option, the non-recessed portions are masked, and the fixation helix 152 is dipped within the drug eluting substance to fill the one or more cavities 180 with the drug eluting substance. The shape and the size of the one or more cavities, types or combinations of drugs can be used to modify the release rate of the drug to be released.

Figure 5A:
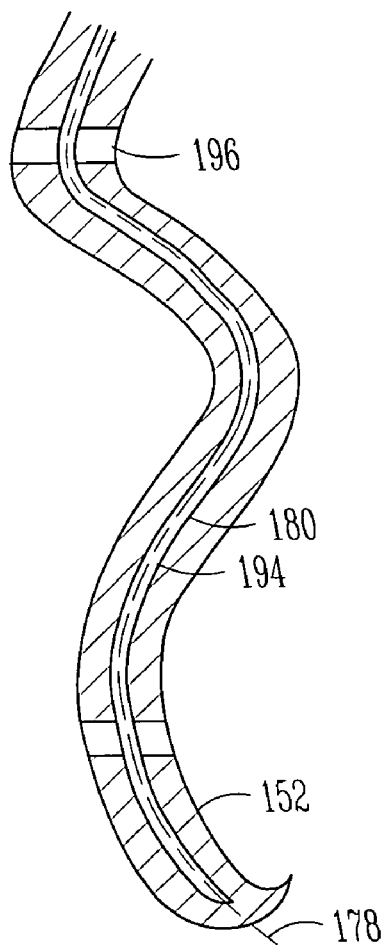
FIG. 5A is a side elevational view of an active fixation assembly constructed in accordance with one embodiment.
Figure 5B:
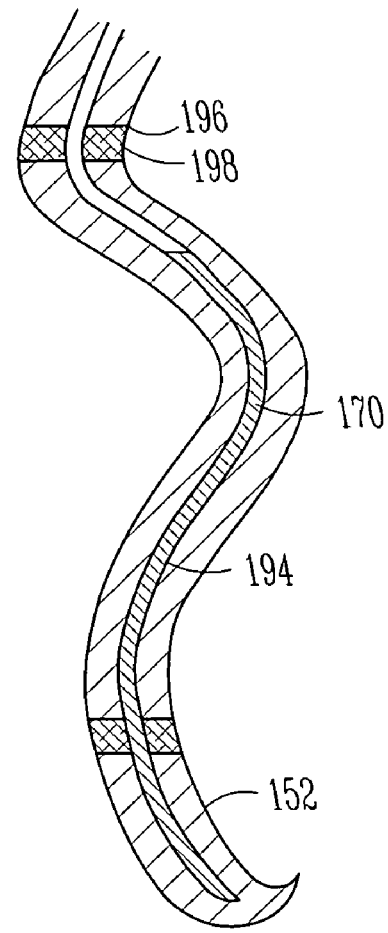
FIG. 5B is a cross-sectional view of the active fixation assembly shown in FIG. 5A.

Referring to FIGS. 5A and 5B, the fixation helix 152 includes one or more cavities 180, and optional drug eluting substance 170 as described above. In one option, the one or more cavities 180 includes a reservoir 194. In one option, the reservoir 194 extends along the helical axis 178. In another option, the reservoir 194 includes a drug eluting substance 170 such as a drug, a drug combination, or a therapeutic agent. The reservoir 194, in one option, can be sized to hold a particular volume of material. In yet another option, the reservoir 194 is provided in addition to passages 196, where the passages 196 extend from an outer surface to the reservoir 194, and allow material from the reservoir 194 to flow out of the fixation helix 152.

In another example, a plug 198 of material is disposed within the passages 196. The plug 198 of material is formed of a material such as borosilicate glass, fused quartz and silica, lead. In addition to the type of material used for the plug, processing conditions, such as laser NA spot size and/or hydrogen firing, can effect the desired premature release of drug eluting substance. The plug material, in one option, prevents premature release of the drug eluting substance 170 disposed within the reservoir 194. The passages 196 include a number of shapes, sizes, configurations, and distribution, including those described above for the one or more cavities 180.

The reservoir 194, in one option, is formed by taking a thin hollow cylinder, such as a hypotube having a lumen therein, and forming the tube into a helical shape. This can be done utilizing cold working and/or heat forming technology. The end of the thin hollow cylinder is closed on one or both ends. The end of the cylinder can be closed, for example, by crimping the end of the cylinder.

Figure 6:
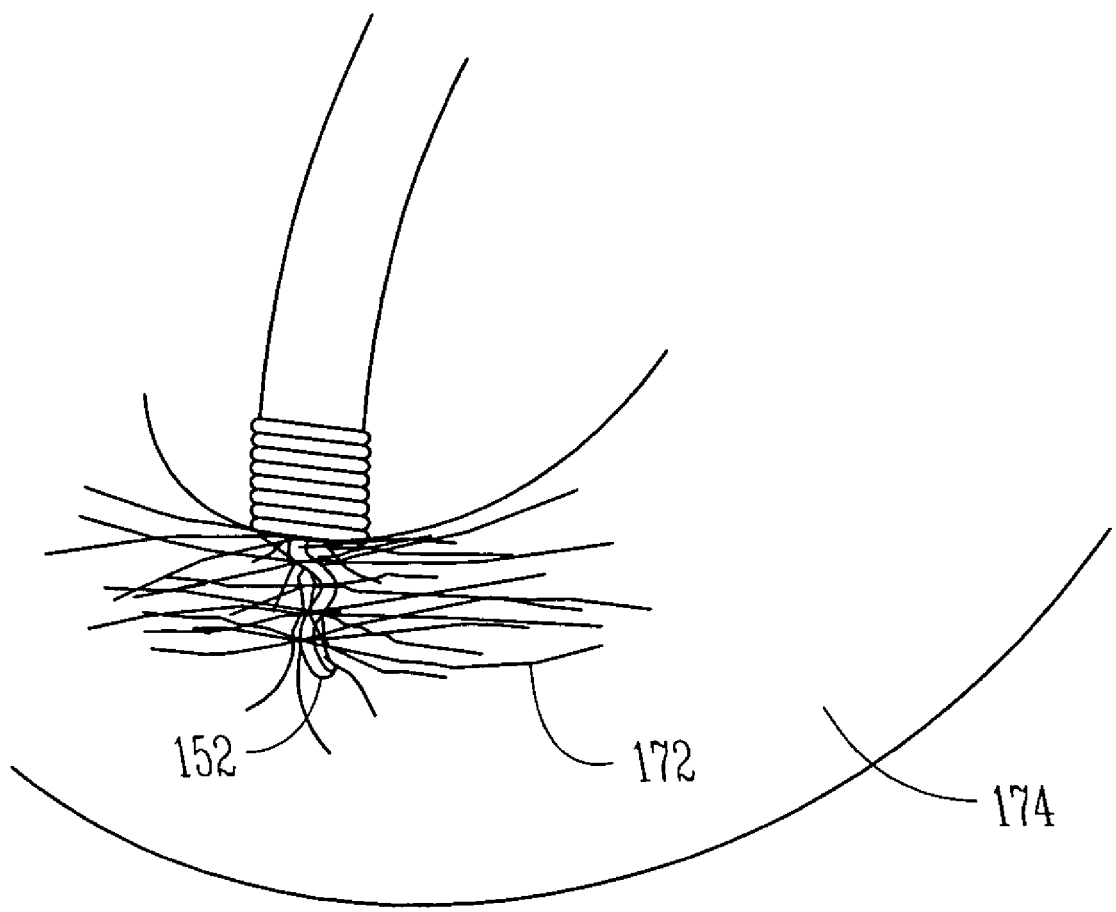
FIG. 6 is a side elevational view illustrating a lead assembly in an implanted position.

FIG. 6 illustrates the fixation helix 152 inserted or engaged with tissue 174. The one or more cavities and/or the reservoir, as discussed above, allow for the drug flow to occur within the tissue 174, such as a wall of a heart, along 172. The drugs flow within the tissue, assisting in reducing tissue inflammation associated with implanting the helix or other devices. The reduced tissue inflammation further assists in lowering the voltage threshold necessary to depolarize and capture heart tissue.

The implantable device allows for drugs to be disposed in close proximity to tissue trauma sites. Furthermore, the implantable device allows for multiple drugs to be delivered, and also provides further options for release rates and/or stages. The cavities, recesses, channels, and/or reservoirs allow for a larger amount or volume of drugs than previously achieved.

It is to be understood that the above description is intended to be illustrative, and not restrictive. Although the use of the implantable device has been described for use as a lead in, for example, a cardiac stimulation system, the implantable device could as well be applied to other types of body stimulating systems or fixation assemblies. Many other embodiments will be apparent to those of skill in the art upon reviewing the above description. The scope should, therefore, be determined with reference to the appended claims, along with the full scope of equivalents to which such claims are entitled.

What is claimed is:

1. An implantable device comprising:
   a device body;
   at least one electrode associated with a portion of the device body;
   at least one conductor electrically coupled with the at least one electrode; and
   an active fixation assembly coupled with a portion of the implantable device, the active fixation assembly having an intermediate portion having one or more pockets therein.

2. The implantable device as recited in claim 1, wherein the active fixation assembly is a fixation helix.

3. The implantable device as recited in claim 2, wherein the fixation helix is the at least one electrode.

4. The implantable device as recited in claim 2, further comprising a drug eluting substance disposed within one or more pockets.

5. The implantable device as recited in claim 1, further comprising an electrical stimulation component electrically coupled with the at least one conductor.

6. The implantable device as recited in claim 1, wherein the device body further includes a housing, the housing including one or more housing cavities therein.

7. The implantable device as recited in claim 6, further comprising a drug eluting substance disposed within the one or more housing cavities.

8. An implantable device comprising:
   a device body;
   at least one conductor disposed within the device body;
   an active fixation assembly coupled with a portion of the implantable device, the active fixation assembly having at least one reservoir therein;
   the active fixation assembly including an outer surface and at least one passage extending from the outer surface to the one or more reservoirs; and
   a plug disposed within the at least one passage.

9. The implantable device as recited in claim 8, further comprising at least one of a drug or a therapeutic agent disposed within the at least one reservoir.

10. The implantable device as recited in claim 9, wherein the one or more reservoirs are self contained within the active fixation assembly.

11. The implantable device as recited in claim 8, wherein the plug includes at least one of a polymer, gel, or glass fit plugs.

12. The implantable device as recited in claim 8, wherein the reservoir has a helical shape.

13. The implantable device as recited in claim 8, wherein the device body is an insulative lead body, and the active fixation assembly is retractable within the device body.

14. The implantable device as recited in claim 8, further comprising an electrical stimulation component electrically coupled with the at least one conductor.

15. The implantable device as recited in claim 8, wherein the active fixation assembly is electrically coupled with the at least one conductor.

16. A method comprising:
   disposing a conductor within an implantable device body;
   electrically coupling a fixation helix with the conductor; and
   forming at least one recess in the helix by removing material from an outer surface of an intermediate portion of the fixation helix.

17. The method as recited in claim 16, further comprising disposing a drug eluting substance within the at least one recess within the helix.

18. The method as recited in claim 17, wherein disposing a drug eluting substance within the at least one recess includes disposing a drug filled glass frit within the helix.

19. The method as recited in claim 16, further comprising electrically coupling the conductor with an electrical stimulation component.

20. The method of claim 16 further comprising forming a hypotube into a helical shape to form the fixation helix.

21. The method of claim 20 further comprising closing at least one end of the hypotube.

22. The method as recited in claim 16, wherein forming at least one recess in the helix includes forming a pocket in the helix.

23. The method as recited in claim 16, wherein removing forming at least one recess in the helix includes forming a passage through the helix.

24. An implantable device comprising:
a device body;
at least one electrode associated with a portion of the device body;
at least one conductor electrically coupled with the at least one electrode; and
an active fixation assembly coupled with a portion of the implantable device, the active fixation assembly having one or more cavities therein, wherein at least one of the one or more cavities extends laterally from a first side of the active fixation assembly to a second side of the active fixation assembly, forming a passage therethrough.

25. The implantable device of claim 24, wherein the active fixation assembly is nontubular.

26. An implantable device comprising:
a device body;
at least one electrode associated with a portion of the device body;
at least one conductor electrically coupled with the at least one electrode; and
an active fixation assembly coupled with a portion of the implantable device, the active fixation assembly including a hypotube having a lumen and one or more pockets.

27. The implantable device of claim 26, wherein the hypotube includes a passage from an outer surface of the hypotube to the lumen in the hypotube.

28. The implantable device of claim 26, further comprising a drug eluting substance in the hypotube.

29. The implantable device of claim 26, wherein the hypotube includes at least one closed end.

30. A method comprising:
forming a hypotube into a helical shape to form a fixation helix
disposing a conductor within an implantable device body;
electrically coupling the fixation helix with the conductor; and
forming at least one recess in the helix by removing material from an outer surface of the fixation helix.

* * * * *

UNITED STATES PATENT AND TRADEMARK OFFICE
CERTIFICATE OF CORRECTION

PATENT NO. : 7,155,292 B2
APPLICATION NO. : 10/671009
DATED : December 26, 2006
INVENTOR(S) : Kawula et al.

It is certified that error appears in the above-identified patent and that said Letters Patent is hereby corrected as shown below:

In column 6, line 41, in Claim 11, delete "fit" and insert -- frit --, therefor.

Signed and Sealed this

Thirteenth Day of March, 2007

JON W. DUDAS
*Director of the United States Patent and Trademark Office*